United States Patent [19]
Allen et al.

[11] Patent Number: 6,080,762
[45] Date of Patent: Jun. 27, 2000

[54] PULMONARY AND NASAL DELIVERY OF RALOXIFENE

[75] Inventors: Darrel LaVern Allen, Indianapolis; Ronald Keith Wolff, Carmel; Paula Ann Leiter; Richard Leon Tielking, both of Knightstown, all of Ind.

[73] Assignee: Eli Lilly and Company, Indianapolis, Ind.

[21] Appl. No.: 09/288,446

[22] Filed: Apr. 8, 1999

Related U.S. Application Data

[60] Provisional application No. 60/081,102, Apr. 8, 1998.

[51] Int. Cl.⁷ .............................. A01N 25/02; A61K 9/14
[52] U.S. Cl. ........................... 514/337; 514/874; 514/951; 514/952; 514/958; 424/43; 424/45; 424/46; 424/489
[58] Field of Search ..................... 514/337, 874, 514/951, 952, 958; 424/489, 43, 45, 46

[56] References Cited

U.S. PATENT DOCUMENTS

| | | | |
|---|---|---|---|
| 4,133,814 | 1/1979 | Jones et al. | 260/326.55 |
| 4,418,068 | 11/1983 | Jones | 424/267 |
| 5,441,965 | 8/1995 | Sall et al. | 514/324 |
| 5,484,798 | 1/1996 | Bryant et al. | 514/324 |
| 5,641,790 | 6/1997 | Draper | 514/333 |
| 5,952,513 | 9/1999 | Palkowitz | 549/52 |

*Primary Examiner*—Frederick Krass
*Attorney, Agent, or Firm*—Gilbert T. Voy

[57] ABSTRACT

The present invention relates to formulations and methods for pulmonary and nasal administration of raloxifene.

30 Claims, No Drawings

PULMONARY AND NASAL DELIVERY OF RALOXIFENE

This application claims the benefit of U.S. Provisional Application No. 60/081,102, filed Apr. 8, 1998.

FIELD OF THE INVENTION

The present invention relates to methods and formulations for pulmonary and nasal administration of raloxifene.

BACKGROUND OF THE INVENTION

Raloxifene is described in U.S. Pat. No. 4,418,068 and is known to be effective in treating the symptoms of post menopausal syndrome, particularly osteoporosis. Indeed, raloxifene hydrochloride was approved for marketing as a preventative treatment for osteoporosis by the U.S. Food and Drug Administration in late 1997.

Raloxifene hydrochloride has the following structure:

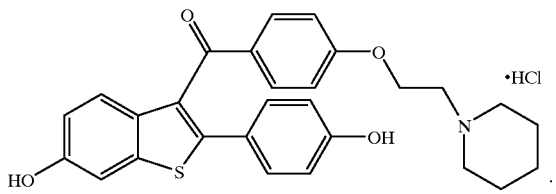

Heretofore, the administration of raloxifene hydrochloride has generally been accomplished orally, i.e., by ingestion of tablets or capsules.

The determination of the lowest effective dose for a pharmaceutical agent is a goal generally of clinical trials. The delivery route and/or formulation of a particular pharmaceutical can significantly effect the size of the lowest effective dose. Administering the least amount of drug which provides the desired effect tends to minimize the possibility of any undesirable side-effects attributed to that pharmaceutical and further provides economic benefits to the drug manufacturer and consumer.

In most cases, relative to oral routes of delivery, respiratory and/or nasal delivery of a drug results in lower blood levels of the pharmaceutical in the recipient. Thus, the lowest effective dose for respiratory tract and nasal delivery is usually higher than for oral delivery. Furthermore, delivery of pharmaceuticals by inhalation into the lungs, or through the nose, is not common because the inhalation of some pharmaceuticals negatively alters the breathing parameters of the recipient.

SUMMARY OF THE INVENTION

The present invention relates to a method for pulmonary delivery of raloxifene to a patient which comprises:
- having the patient inhale an aerosolized amount of raloxifene through the patient's mouth into the lungs; and
- optionally repeating the inhalation step a sufficient number of times until an effective amount of raloxifene is delivered to the patient.

In addition, the present invention relates to a method for the nasal delivery of raloxifene to a patient which comprises:
- having the patient inhale an aerosolized amount of raloxifene through and into the patient's nose; and
- optionally repeating the inhalation step a sufficient number of times until an effective amount of raloxifene is delivered to the patient.

Furthermore, the present invention relates to a pharmaceutical formulation comprising raloxifene dissolved or suspended in a pharmaceutical solvent at a concentration between 1 mg/mL and 100 mg/mL, optionally in the presence of one or more preservatives, surfactants or gases, said formulation suitable for nebulization or spraying.

Moreover, the present invention relates to a pharmaceutical formulation comprising raloxifene present as a dry powder, with a mass median equivalent aerodynamic diameter between 0.5 $\mu$m and 100 $\mu$m, in an aerosol propellant, optionally in the presence of ethanol, said formulation suitable for use in a metered dose inhaler.

The methods of the present invention provide for an unexpected high level of bioavailability of raloxifene which results from delivery of raloxifene via the nose and/or lung.

DETAILED DESCRIPTION OF THE INVENTION

When "raloxifene" is referred to it is understood that such a term refers especially to raloxifene hydrochloride but such a term also includes other salts and solvates thereof.

The terms "pulmonary delivery" and "respiratory delivery" refer to systemic delivery of raloxifene to a patient by inhalation through the mouth and into the lungs.

The term "nasal delivery" refers to systemic delivery of raloxifene to a patient by inhalation through and into the nose.

The term "patient" refers to a mammal, particularly a human female, that is in need of raloxifene. A preferred need arises in human menopausal females who are either suffering from, or likely to suffer from, osteoporosis. The use of raloxifene to inhibit osteoporosis is well described in U.S. Pat. Nos. 5,393,763, 5,457,117, 5,478,847, 4,698,328, the disclosures of each are incorporated herein by reference. Other uses (needs) for raloxifene and pathological conditions susceptible to inhibition by raloxifene are set out at least in U.S. Pat. Nos. 5,389,670, 5,391,557, 5,393,763, 5,441,966, 5,446,053, 5,447,941, 5,451,589, 5,457,113, 5,447,116, 5,464,845, 5,478,847, 5,502,074, 5,510,370, 5,534,526, 5,552,416, 5,571,808, 5,593,987, 5,610,168, and 5,698,572, the teachings of each are herein incorporated by reference.

As used herein, the term "effective amount" means an amount of raloxifene which is capable of inhibiting the various pathological conditions herein described, e.g., osteoporosis.

The terms "inhibit" and "inhibiting" bear their usual meaning which includes prohibiting, treating, alleviating, ameliorating, halting, restraining, slowing or reversing the progression, or reducing the severity of a pathological condition described above. As such, these methods include both medical therapeutic (acute) and/or prophylactic (prevention) administration as appropriate.

The term "pharmaceutical", when used as an adjective herein, means substantially non-toxic to the patient.

The present invention relates to methods for the pulmonary and/or nasal delivery of raloxifene to a mammalian patient, preferably to a human patient, and pharmaceutical formulations adapted for said pulmonary and nasal delivery. The methods of the present invention are carried out by dispersing an amount of raloxifene in a volume of gas to produce an aerosolized amount. The dispersion may be produced by the patient's inspiratory breath, by introducing a dry powder of raloxifene into a high velocity gas stream, by nebulizing or spraying a liquid solution or suspension of raloxifene, or by releasing a propellant containing raloxifene through a nozzle. The patient inhales the aerosolized amount through the mouth and/or through the nose into the lungs and/or nose. By repeating the dispersing and inhaling steps a sufficient number of times, a desired total dosage (an effective amount) of raloxifene can be delivered to the patient.

Raloxifene may be made by established procedures, such as those detailed in U.S. Pat. Nos. 4,418,068 and 5,629,425, the teachings of which are herein incorporated by reference. Particular formulations of raloxifene suitable for respiratory or nasal delivery to a patient include dry powders, liquid solutions or suspensions suitable for nebulization or spraying, and propellant formulations suitable for use in metered dose inhalers (MDI's). The preparation of such formulations is well described in the patent, scientific, and medical literatures, and the following Examples.

The major difference between a respiratory formulation versus nasal is that the raloxifene particle size requirement is not as limited for nasal delivery as it is for respiratory delivery. In fact, the operable particle size range for a respiratory formulation is a subset of the operable particle size range for nasal formulation. Therefore, simpler devices can frequently be used, e.g., nasal pump sprayers, to deliver raloxifene nasally.

The following discussion of formulations suitable for nasal and/or lung delivery is not meant to be limiting in any way as the practice of the present invention is not dependent upon a particular type of nasal and/or lung delivery formulation/system.

Dry powder formulations will typically comprise raloxifene in a dry, usually lyophilized, form of an appropriate particle size or within an appropriate particle size range. Minimum particle size appropriate for deposition within the lung is typically 0.5 $\mu$m mass median equivalent aerodynamic diameter (MMEAD), but is preferably 1 $\mu$m MMEAD, and is most preferably 2 $\mu$m MMEAD. Maximum particle size appropriate for deposition within the lung is typically 10 $\mu$m MMEAD, but is preferably 8 $\mu$m MMEAD, and is most preferably 4 $\mu$m MMEAD. A particle size of about 3 $\mu$m MMEAD is most preferred. Minimum particle size appropriate for deposition within the nose is typically 0.5 $\mu$m MMEAD, but is preferably 3 $\mu$m MMEAD, and is most preferably 5 $\mu$m MMEAD. Maximum particle size appropriate for deposition within the nose is typically 100 $\mu$m MMEAD, but is preferably 50 $\mu$m MMEAD, and is most preferably 20 $\mu$m MMEAD. Respirable powders of raloxifene within the preferred size range can be produced by a variety of conventional techniques, such as jet milling, spray drying, solvent precipitation, supercritical fluid condensation, and the like. Because particle size is less important for nasal delivery, crystallization from solution may be sufficient. If it is not sufficient, it could be augmented by jet milling or ball milling.

These dry powders of appropriate MMEAD can be administered to a patient via a conventional dry powder inhalers (DPI's) which rely on the patient's breath, upon inhalation, to disperse the power into an aerosolized amount. Alternatively, the dry powder may be administered via air assisted devices that use an external power source to disperse the powder into an aerosolized amount, e.g., a piston pump.

Dry powder devices typically require a powder mass in the range from about 1 mg to 20 mg to produce a single aerosolized dose ("puff"). If the required or desired dose of raloxifene is lower than this amount, as discussed below, the raloxifene powder will typically be combined with a pharmaceutical dry bulking powder to provide the required total powder mass. Preferred dry bulking powders include sucrose, lactose, dextrose, mannitol, glycine, trehalose, human serum albumin (HSA), and starch. Other suitable dry bulking powders include cellobiose, dextrans, maltotriose, pectin, sodium citrate, sodium ascorbate, and the like.

When the dry powder is prepared by solvent precipitation, buffers and salts are typically used to stabilize the raloxifene in solution prior to particle formation. Suitable buffers include, but are not limited to, ascorbate, phosphate, citrate, acetate, and tris-HCl, typically at concentrations from about 5 mM to 50 mM. Suitable salts include sodium chloride, sodium carbonate, calcium chloride, and the like.

Liquid formulations of raloxifene for use in a nebulizer system, e.g., compressed air-, jet-, ultrasonic-, and piezoelectric nebulizers, can employ raloxifene dissolved or suspended in a pharmaceutical solvent, e.g., water, ethanol, or a mixture thereof. Typically, the minimum concentration of raloxifene dissolved/suspended is about 1 mg/mL, but is preferably 5 mg/mL, and is most preferably 10 mg/mL. Generally, the maximum concentration of raloxifene dissolved/suspended is about 100 mg/mL, but is preferably 60 mg/mL, and is most preferably 20 mg/mL. The total volume of nebulized liquid needed to deliver the aerosolized amount is generally in the range from about 0.1 mL to 5 mL.

The pharmaceutical solvent employed can also be a slightly acidic aqueous buffer (pH 4–6). Suitable buffers are as described above. Other components may be added to enhance or maintain chemical stability, including preservatives, surfactants, dispersants, or gases. Suitable preservatives include, but are not limited to, phenol, methyl paraben, paraben, m-cresol, thiomersal, benzylalkonimum chloride, and the like. Suitable surfactants include, but are not limited to, oleic acid, sorbitan trioleate, polysorbates, lecithin, phosphotidyl cholines, and various long chain diglycerides and phospholipids. Suitable dispersants include, but are not limited to, ethylenediaminetetraacetic acid, and the like. Suitable gases include, but are not limited to, nitrogen, helium, carbon dioxide, air, and the like.

Sprayer systems for respiratory and/or nasal delivery of raloxifene employ formulations similar to that described for nebulizers. For a description of such lung systems and others described herein, see e.g., Wolff, R. K. and Niven, R. W., "Generation of Aerosolized Drugs," *J. Aerosol Med.*, 7:89, 1994. Nasal delivery systems have been described in *Transdermal Systemic Medication*, Y. W. Chien Ed., Elsevier Publishers, New York, 1985 and in U.S. Pat. No. 4,778,810, the teachings of which are herein incorporated by reference.

For use in MDI's, raloxifene may be dissolved or suspended in a suitable aerosol propellant, such as a chlorofluorocarbon (CFC) or a hydrofluorocarbon (HFC). Such suspensions will contain between 10 mg to 100 mg of raloxifene per aerosol dose. Suitable CFC's include trichloromonofluoromethane (propellant 11), dichlorotetrafluoromethane (propellant 114), and dichlorodifluoromethane (propellant 12). Suitable HFC's include tetrafluoroethane (HFC-134a) and heptafluoropropane (HFC-227).

For incorporation into the aerosol propellant, raloxifene is preferably processed into particles of the sizes described above for the dry powder formulations. The particles may then be suspended in the propellant as is, but are typically coated with a surfactant to enhance/facilitate their dispersion. Suitable surfactants are as defined above for liquid formulation. A propellant formulation may further include a lower alcohol, such as ethanol (up to 30% by weight) and other additives to maintain or enhance chemical stability and physiological acceptability. Additives suitable for propellant formulations include a surfactant as described above, such as sorbitals, oleic acid, and lecithins. For further information on such addivitives, see G. W. Hallworth. "The formulation and evaluation of pressurised metered-dose inhalers," *Drug Delivery to the Lung*, D. Ganderton and T. Jones (eds), Ellis Horword, Chichester, U.K., pg's 87–118.

The precise dosage of raloxifene necessary will vary with the age, size, sex and condition of the subject, the nature and severity of the disorder to be treated, and the like; thus, a precise effective amount should be determined by the caregiver.

However, the total aerosolized dosage of raloxifene for the treatment of osteoporosis will typically be in the range from about 2 mg to 16 mg/per day, usually being in the range from about 4 mg to 8 mg/per day. Such dosages will result in a total systemic availability (i.e., amount which is delivered to the blood) in the range from about 0.5 mg to 5 mg/per day, usually from 1 mg to 2.5 mg/per day. Precise dosages will, of course, vary depending on known pharmacokinetic factors and the individual characteristics of the inhaler system (see particularly the discussion of MDI's below). Usually, the total dosage of raloxifene will be delivered in a few separate aerosolized doses, typically being from 1 to 3, and most typically 1 to 2, where each aerosolized amount contains from 1 mg to 8 mg of raloxifene.

In the case of a dry powder formulation or a liquid formulation suitable for use in a nebulizer or sprayer, a total dosage of raloxifene within the above ranges can be achieved with one or more aerosolized amounts inhaled by the patient.

Because of the inefficiencies of MDI devices, only a small portion, typically in the range of 5% to 20%, of the drug will reach the lungs. Thus, an effective amount of raloxifene can be delivered in from two to five aerosolized amounts, with about 20 mg of raloxifene being in each of the amounts.

The following Working Example further illustrates the practice of the present invention but is not intended to be limiting to the scope of the invention in any respect, and should not be so construed.

WORKING EXAMPLE 1

The cynomolgus monkey has been found to be a good pharmacokinetic model for the metabolism and disposition of raloxifene in humans. Aerosol deposition of a pharmaceutical through the lung and nose in monkeys is similar to that in humans. Schlesinger, R. B., "Comparative Deposition of Inhaled Aerosols in Experimental Animals and Humans: A Review," *J. Toxicol. Environ. Health*, 15:197, 1985. In addition, nasal anatomy and mucociliary clearance is similar in monkeys compared to man (Wolff, et al., "*Nasal Clearance in Rhesus Monkeys,*" *J. Aerosol Medicine*, 6:111–119, 1993).

Six adult cynomolgus monkeys (three males and three females) were used for this study. Males weighed from 5.3 kg to 5.5 kg at the start of the live phase. Females weighed from 3.8 kg to 4.9 kg at the start of the live phase. Each animal was uniquely identified with a number tattooed on the inner thigh.

The animals were housed individually in stainless steel cages. Rooms were thermostatically set to maintain a temperature of 72° F. and maintain an actual temperature within 8° F. from that set point. The environmental control system is designed to maintain a relative humidity of 20% and a maximum of 80%. Light was on a 12 hour cycle, with lights on between 0600 and 1800. Animals were fed twice daily with Purina Certified Primate Chow No. 5048, except on test days. On test days, the animals were given primate chow only after the completion of the inhalation exposures. Water was available ad libitum except during exposure times.

Prior to beginning the live phase of the study, the monkeys were conditioned, over an approximately 3 month period, to be caught, handled, and placed in a restraint chair using the pole-and-collar method. Foods like peanuts, marshmallows, and a variety of dried and fresh fruits were used as training rewards. The time that the monkeys were left in the chair was increased gradually up to 8 hours. By the end of the training period, all the monkeys could be caught quickly, placed into the restraint chair easily, and would allow limb manipulation, including having blood drawn, while in the chair.

Each monkey was studied once per week for 5 weeks. Target concentrations of raloxifene activity were 0, 3, 10, 0, and 30 $mg/m^3$ for Weeks 1 through 5 respectively. The activity was determined by correcting the amount of raloxifene collected by the potency of the lot used. Each exposure was for 8 hours, divided into 4 hour segments with 15 minutes in between. During the 15 minute period between the 4 hour exposures, the monkeys were offered juice to drink and apple pieces to eat. The conditioning period described above had used this method to keep the animals from becoming agitated due to hunger or thirst. A 15 minute break in the exposures was not expected to affect the blood levels of raloxifene.

The monkeys were placed into the restraint prior to each exposure. Two sheets of latex (0.030 in. thick) were placed around the animal's necks to form a seal. A 7-L head dome was placed over the animal's heads as described in *J. Appl. Toxicol.*, 15:13, 1995. Airflow of 15 L/min was maintained through the head dome via a calibrated transvector on the exhaust port. The raloxifene was aerosolized using a Wright Dust Feed II. The generated aerosol passed through a cyclone (*Environ. Sci. Technol.*, 13:1387, 1979) designed to eliminate, using inertial properties, particles larger than 2 $\mu$m MMEAD. The aerosol then entered the head-dome for the monkey to breath. For compounds with molecular weights smaller than most proteins, including raloxifene, particles of these sizes will deposit both in the nose and the lungs and absorption will take place from both of these sites. Bond, S. W., *Drug Delivery to the Respiratory Tract*, D. Ganderton and T. Jones (eds), Ellis Horwood Publishers, Chichester, U.K., pgs. 133–139, 1987.

Each day, before the monkeys were exposed, the exposure system was set up and a gravimetric sample was taken to determine the raloxifene concentration. The monkey was then placed in the chair and the aerosol was generated using the same generator settings. After the exposure to the monkey, it was removed from the chair, the system re-assembled, and another gravimetric sample taken. The concentrations derived from the 2 gravimetric samples were averaged to obtain the raloxifene concentration for that exposure. Gravimetric concentrations were determined by collecting the aerosol directly from the head-dome onto a 25 mm Gelman type A/E glass fiber filter. The airflow drawn through the filter was 1 L/min with sample times of 1 hour for the 3 $mg/m^3$ exposures and 20 minutes for the 10 and 30 $mg/m^3$ exposures. One particle size determination was done for each exposure concentration. The particle size was determined from samples collected using a Sierra Model 218K Cascade Impactor fitted with Gelman Type A/E glass fiber filters. Airflow through the Cascade Impactor was 3 L/min with sample times of 1143, 300, and 115 minutes for the 3,10, and 30 $mg/m^3$ exposures, respectively.

During the raloxifene exposures, 5 mL of blood were collected from the femoral artery or vein at the following approximate times after the beginning of exposure: pre-exposure, 1, 2, 4, 8, 11, and 14 hours. The blood was collected in heparinized tubes. To obtain the plasma, each tube was centrifuged at 200 xg for 15 minutes at 4° C. or 10° C. The top 1 mL of plasma was removed, and the remaining plasma was placed in tubes and stored at −70° C. until sent for assay of raloxifene concentrations.

Breathing patterns (tidal volume, breathing frequency, and minute volume) were monitored using a size '0' pneumotachograph connected to a port on the head-dome. The signals were collected on a personal computer using the LS20 software from Buxco Electronics, Inc. At least 10 minutes of pre-exposure data were collected before the exposures began, followed by data collection throughout the 8-hour exposure period. Pre-exposure data were collected as 1-minute averages and exposure data were collected as 5-minute averages.

The AUC ratios of raloxifene/total raloxifene in the 10 and 30 mg/m$^3$ dose groups were 0.56 and 0.82 respectively. (See Table 1 below.) The AUC ratios of raloxifene/total raloxifene in this inhalation study are substantially different than those observed in a similar study after oral administration of raloxifene to cynomolgus monkeys in which values of 0.02 to 0.04 were observed. As a consequence, the total amount of raloxifene required by this route of administration, to place an effective amount of raloxifene in a patient's blood, would be substantially less than by oral delivery. No appreciable sex differences in raloxifene, total raloxifene, Cmax, or AUC values were observed. In addition, no significant changes in tidal volume or breathing frequency occurred during any of the exposures. Some data collected in carrying out the experiment of Example 1 is illustrated in Table 1 below.

TABLE 1

| Exposure Conc. (mg Ralox./m$^3$ of air) | Cmax (Mean Ralox. in ng/mL) | Cmax (Mean Tot. Ralox. in ng/mL) | AUC |
| --- | --- | --- | --- |
| 3.3 | 7 | * | * |
| 9.7 | 17 | 10 | 0.56 |
| 26.9 | 47 | 84 | 0.82 |

* Values too low for accurate measurement

Relative to oral delivery, both nasal and lung delivery result in reduced first pass liver metabolism of a pharmaceutical. Blood from the nose is taken by the venous system to the heart and then it is distributed to the body. Material deposited in the lung is absorbed into capillary blood, and then to the heart. Accordingly, the pulmonary/nasal route of exposure employed in Example 1, resulted in higher, relative to oral delivery, initial levels of unmetabolized raloxifene absorbed into the blood. However, because about 20% of the blood flows from the heart to the liver one would expect that liver metabolism would rapidly decrease the blood levels of raloxifene to values similar to those following oral delivery. Surprisingly, the pulmonary/nasal delivery of raloxifene to six adult cynomolgus monkeys described above resulted in relatively higher blood levels of raloxifene which lasted for several hours. Those blood levels obtained by pulmonary/nasal delivery were considerably higher than those obtained following oral administration at an equivalent dose.

These results demonstrate that the methods of the present invention provide for an unexpected high level of bioavailability of raloxifene. This greater bioavailability can translate into economic benefits for the patient/manufacturer and can provide an advantageous safety profile relative to higher dose formulation/delivery methods.

We claim:

1. A method for pulmonary delivery of raloxifene to a patient which comprises:
    having the patient inhale an aerosolized amount of raloxifene through the patient's mouth into the lungs; and
    optionally repeating the inhalation step a sufficient number of times until an effective amount of raloxifene is delivered to the patient.

2. The method according to claim 1 where the raloxifene is raloxifene hydrochloride.

3. The method according to claim 2 where the patient is a human female.

4. The method according to claim 3 where the areosolized amount is produced by introducing raloxifene as a dry powder, optionally in the presence of a bulking agent, into a gas stream.

5. The method according to claim 4 where the gas stream is the patients' inspiratory breath.

6. The method according to claim 3 where the aerosolized amount is produced by nebulizing or spraying a liquid solution or suspension of raloxifene.

7. The method according to claim 4 where the aerosolized amount contains from about 1 mg to about 8 mg of raloxifene and the total dosage is from about 2 mg to about 16 mg per day.

8. The method according to claim 6 where the aerosolized amount contains from about 1 mg to about 8 mg of raloxifene and the total dosage is from about 2 mg to about 16 mg per day.

9. The method according to claim 3 where the aerosolized amount is produced by releasing a propellant containing raloxifene as a dry powder.

10. The method according to claim 9 where the aerosolized amount contains from about 10 mg to about 100 mg of raloxifene.

11. A method for the nasal delivery of raloxifene to a patient which comprises:
    having the patient inhale an aerosolized amount of raloxifene through and into the patient's nose; and
    optionally repeating the inhalation step a sufficient number of times until an effective amount of raloxifene is delivered to the patient.

12. The method according to claim 11 where the raloxifene is raloxifene hydrochloride.

13. The method according to claim 12 where the patient is a human menopausal or post menopausal female.

14. The method according to claim 13 where the areosolized amount is produced by introducing raloxifene as a dry powder, optionally in the presence of a bulking agent, into a gas stream.

15. The method according to claim 14 where the gas stream is the patients' inspiratory breath.

16. The method according to claim 13 where the aerosolized amount is produced by nebulizing or spraying a liquid solution or suspension of raloxifene.

17. The method according to claim 14 where the aerosolized amount contains from about 1 mg to about 8 mg of raloxifene and the total dosage is from about 2 mg to about 16 mg per day.

18. The method according to claim 16 where the aerosolized amount contains from about 1 mg to about 8 mg of raloxifene and the total dosage is from about 2 mg to about 16 mg per day.

19. The method according to claim 13 where the aerosolized amount is produced by releasing a propellant containing raloxifene as a dry powder.

20. The method according to claim 19 where the aerosolized amount contains from about 10 mg to about 100 mg of raloxifene.

21. A pharmaceutical formulation comprising raloxifene dissolved or suspended in a pharmaceutical solvent at a concentration between 1 mg/mL and 100 mg/mL, optionally in the presence of one or more preservatives, surfactants or gasses, and means for nebulization or spraying.

22. The formulation according to claim 21 where the raloxifene is raloxifene hydrochloride.

23. The formulation according to claim 22 where the raloxifene is present at a concentration in the range from 5 mg/mL to 60 mg/mL.

24. The formulation according to claim 23 where the concentration range is from 10 mg/mL to 20 mg/mL.

25. A pharmaceutical formulation comprising raloxifene present as a dry powder, with a mass median equivalent aerodynamic diameter between 0.5 $\mu$m and 100 $\mu$m, in an aerosol propellant, optionally in the presence of ethanol, said formulation suitable for use in a metered dose inhaler.

26. The formulation according to claim 25 where the raloxifene is raloxifene hydrochloride.

27. The formulation according to claim 26 where the raloxifene has a mean particle size in the range from 1 $\mu$m to 8 $\mu$m.

28. The formulation according to claim 27 where the mean particle size is in the range from 2 $\mu$m to 4 $\mu$m.

29. The formulation according to claim 26 where the raloxifene has a mean particle size in the range from 3 $\mu$m to 50 $\mu$m.

30. The formulation according to claim 29 where the mean particle size is in the range from 5 $\mu$m to 20 $\mu$m.

* * * * *